United States Patent [19]
Georgiades et al.

[11] Patent Number: 5,762,962
[45] Date of Patent: Jun. 9, 1998

[54] ANTACID PHARMACEUTICAL COMPOSITION

[75] Inventors: Constantine Georgiades, East Brunswick; R. Michael Buch, Randolph; E. Eric Engelman, Budd Lake; Frank A. Volpe, Kinnelon, all of N.J.

[73] Assignee: Warner-Lambert Company, Morris Plains, N.J.

[21] Appl. No.: 316,416

[22] Filed: Oct. 5, 1994

[51] Int. Cl.⁶ ............... A61K 9/46; A61K 9/20; A61K 47/30; A01N 25/34

[52] U.S. Cl. ............... 424/466; 424/465; 514/772.3; 514/777; 514/781; 514/782

[58] Field of Search ............... 424/465, 466; 514/772.3, 777, 781, 782

[56] References Cited

U.S. PATENT DOCUMENTS 3,384,546  5/1968  Palermo .
3,621,094  11/1971  Mayron .
5,503,846  4/1996  Wehling et al. ............... 424/466

FOREIGN PATENT DOCUMENTS

B-17614/92  4/1991  Australia .
B-44883/93  3/1994  Australia .
922038  4/1963  United Kingdom .
1056212  2/1965  United Kingdom .
WO 94/12207  6/1994  WIPO .

*Primary Examiner*—Carlos Azpuru
*Attorney, Agent, or Firm*—Jean B. Barish

[57] ABSTRACT

Antacid pharmaceutical compositions provide optimal buffering profiles of from 3.0 to 5.0 for immediate and long lasting relief from the symptoms of acid indigestion, sour stomach, heartburn and gas. The composition may comprise a dual or tripartite combination of the actives calcium carbonate, calcium or magnesium citrate and/or calcium phosphate which, as a result of their different activities, neutralize the excess stomach acid both immediately and continuously over time. The formulations also provide the individual with alternative dosage forms which may provide greater levels of calcium, less sodium and less production of gastrointestinal gas.

22 Claims, 4 Drawing Sheets

ANTACID PHARMACEUTICAL COMPOSITION

BACKGROUND OF THE INVENTION

The present invention relates generally to pharmaceutical compositions comprising active agents useful in the treatment of upper gastrointestinal disorders such as what is commonly referred to as sour stomach, upset stomach, heartburn, gas, acid indigestion and the like. Pharmaceutical compositions containing antacid agents useful for treating gastrointestinal problems are widely used and have been around for quite some time. They vary to some extent in the active ingredients and other excipients and increasingly vary with respect to the other ingredients used that are responsible for flavor, texture, mouthfeel and mechanisms of delivery.

Ingestible pharmaceutical agents capable of relieving gastrointestinal distress typically work by neutralizing stomach acid. Predominantly, these antacids comprise a carbonate or hydroxide of an alkaline earth metal salt such as calcium carbonate or magnesium hydroxide. In terms of simple chemistry, using calcium carbonate as an example, the neutralization reaction occurs as follows $$H^+(acid)+CaCO_3 \rightarrow HCO_3^- + Ca^{++} \qquad 1.$$

$$H^+ + HCO_3^- \rightarrow H_2O + CO_2 \uparrow \qquad 2.$$

These agents unfortunately also present a chalky, gritty mouthfeel which must somehow be taste-masked in order to insure good patient compliance. Whereas certain levels of the active agent are needed in order to achieve the optimal buffering profile of pH 3.0–5.0, large amounts of the metal salt in the tablet or liquid dosage form can substantially detract from its palatability. A happy medium is required then, that provides both quick, upfront and sustained relief while at the same time is incorporated in the delivery system at levels that do not render the medication bad tasting.

U.S. Pat. No. 3,621,094 to Mayrom et. al. discloses an aqueous pharmaceutical composition for the treatment of acid indigestion and ulcers comprising a high concentration of antacid and a combination of monobasic calcium phosphate and a non-toxic alkali metal or alkaline gluconate salt such as sodium, potassium, calcium and the like. It is asserted that the use of monobasic calcium phosphate and the gluconate salt permits the incorporation of higher levels of antacid than previously possible. These high levels of antacid are particularly necessary in the treatment of peptic ulcers. It is asserted that the composition is effective in reducing gastrointestinal discomfort while at the same time affording the patient a palatable tablet form.

U.S. Pat. No. 4,786,502 to Chapura et. al. discloses palatable pharmaceutical compositions useful in the treatment of gastrointestinal disorders comprising a bismuth or metallic antacid salt such as calcium carbonate or aluminum phosphate, a lipid material with a melting point of from about 26° C. to about 37° C., a hydrophilic dispersant such as a sugar alcohol and an emulsifier. The compositions allegedly allow for the incorporation of sufficiently high amounts of the active for quick and long lasting relief while at the same time providing for a good tasting, smooth textured means of delivery.

U.S. Pat. No. 3,573,006 to Shik et. al. discloses an antacid composition comprising a polymeric aluminum and magnesium hydroxy complex in a pharmaceutically acceptable carrier for the relief of stomach acid distress, and is allegedly pleasant tasting with a non-gritty mouthfeel.

U.S. Pat. No. 4,495,087 to Wright et. al. teaches a palatable antacid consisting of an aluminum hydroxycarbonate gel that is effective in buffering high levels of stomach acid.

Finally, U.S. Pat. No. 4,592,039 to Duvall et. al. discloses an effervescent analgesic antacid with reduced sodium content for those who must restrict their sodium intake. Aspirin, acetaminophen, ibuprofen and the like are combined with an antacid selected from the group consisting of citric acid, sodium bicarbonate, calcium carbonate, potassium bicarbonate and other fillers, flavors and sweeteners.

It is relatively clear then that there have been many formulations in the past developed to reduce gastrointestinal distress that utilize metal salts such as calcium carbonate, dihydroxy aluminum sodium carbonate (DASC), calcium phosphate, sodium citrate, magnesium carbonate, monobasic calcium phosphate aluminum carbonate, aluminum hydroxide and the like. Few of these however, have been able to provide an antacid that is both fast acting for immediate upfront relief, long lasting for sustained relief and yet good tasting with a palatable mouthfeel. Whereas DASC formulations are able to achieve optimal buffering, few have provided an optimal buffering profile of from about 3.0 to about 5.0 pH both quickly and for long periods of time, yet also taste good when administered. And whereas on the one hand they provide relief by neutralizing the stomach acid, the subsequent evolution of $CO_2$ gas can unfortunately result in another form of discomfort for many.

SUMMARY OF THE INVENTION

The present invention is a pharmaceutical composition comprising an antacid that provides both immediate, intermediate, and long lasting relief while being low in sodium, aluminum-free and yet possessing a good taste and mouthfeel when administered. The composition contains calcium carbonate in combination with another buffer such as calcium or magnesium citrate, and/or calcium phosphate and mixtures thereof and thereby may also provide a dietary supplement of calcium while offsetting the prevention of phosphate absorption by providing additional phosphate. In a preferred embodiment, a tripartite formulation of calcium carbonate, calcium citrate and calcium phosphate provides both up-front, immediate acid neutralization that is also a sustained long lasting relief without over-compensating to highly basic pH levels. Low in sodium and aluminum-free, these formulations provide not only a source of calcium but generate little gas by utilizing other non-carbonate buffers. The antacid formulation provides optimal acid neutralizing capability and may also comprise other standard antacid filler and flavor ingredients as desired to prepare either a liquid or solid dosage form.

DETAILED DESCRIPTION OF THE INVENTION

Figure 1:
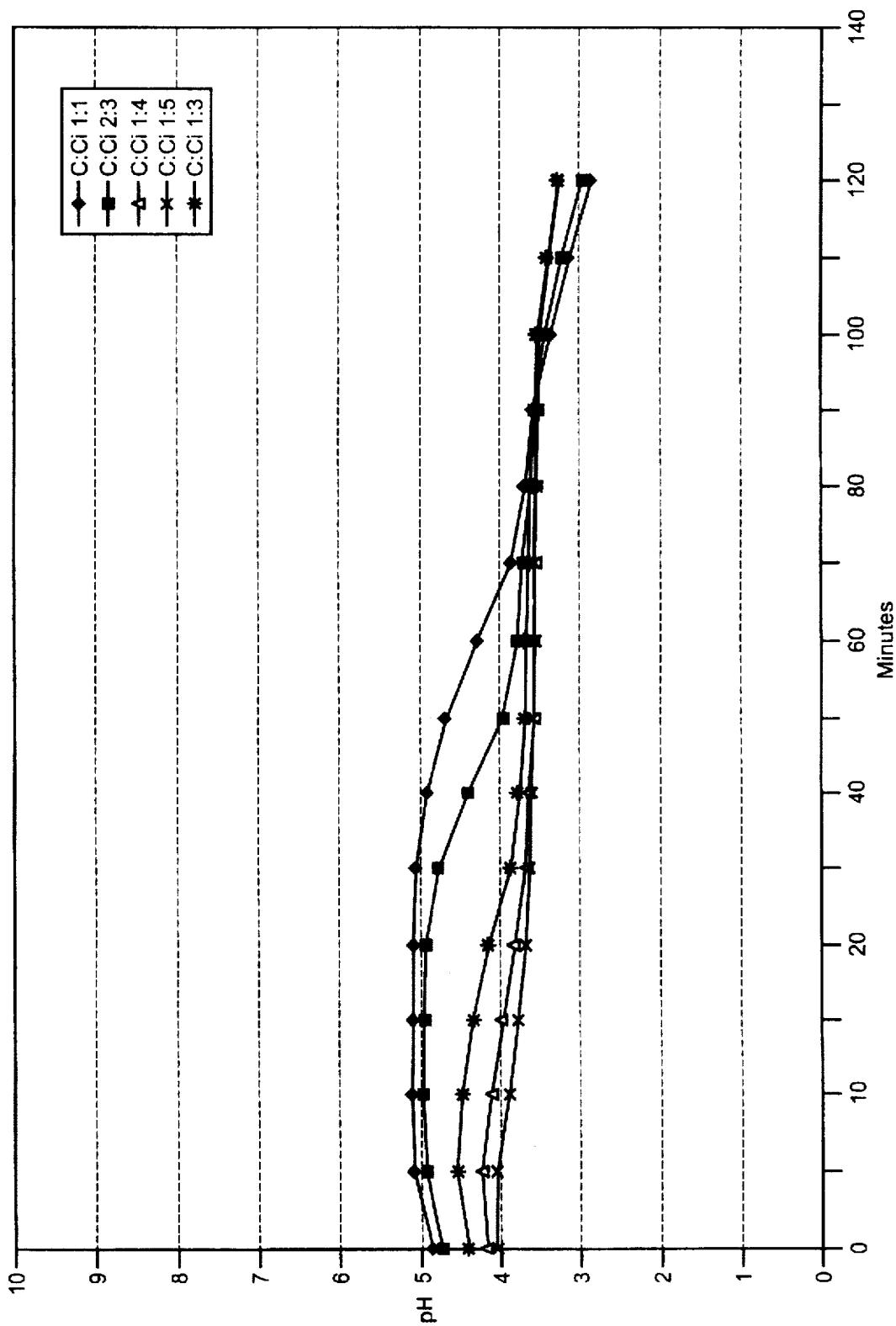
FIG. 1 is a graph depicting the continuous acid challenge profile of calcium carbonate/calcium citrate formulations of the present invention as a function of pH versus time.

Antacids and other similar gastrointestinal medications relieve symptoms such as the burning, painful sensation of heartburn and indigestion through neutralization of acid formed in the stomach. Few antacids are available however, that afford both immediate, upfront relief and sustained, long lasting relief over time. It is well known that the ideally neutralized stomach environment is at a pH of from about 3.0 to about 5.0, and it is when acid buildup lowers the pH below 3.0 that mucosal erosion, the pain of heartburn, acid indigestion and associated discomfort sets in. Obviously then, a rapid correction and maintenance of the stomach pH in this optimal realm will alleviate most discomfort.

The formulations of the present invention are based upon the theory that the buffering profile of a mix of ingredients with different solubilities will provide acid neutralization action at different times and hence will result in overlapping pH profiles. The ability of a medication to relieve the symptoms associated with heartburn, sour stomach, and acid indigestion is measured in terms of its acid neutralizing capacity (ANC) and is a function of its ability to maintain the stomach at conditions with pH values of from about 3.0 to about 5.0 over time. The formulations of the present invention were discovered to surprisingly and unexpectedly neutralize strongly acidic conditions to this range immediately upon consumption and for extended periods of time. For example, calcium carbonate ($CaCO_3$) provides substantially long lasting, sustained action relief. Its onset is more delayed and slower than that of the other more soluble components. Calcium citrate provides substantially greater up-front and immediate release so that the two, when combined together provide a broader spectrum of acid neutralizing therapy.

The acid neutralizing capacity for each buffer varies and hence the amount of buffer incorporated in an antacid dosage form is dependent upon the relative ANC's for each component. As used herein, the amount of buffer used in the claimed formulations will be defined in terms of its ANC and the amount contributed by a component as a percentage of the total.

Calcium carbonate has an acid neutralizing capacity of 20 per gram; that is, one (1) gram of calcium carbonate will neutralize 20 (mls.) of 1N acid or 20 meq. thereof. Calcium citrate has an ANC of 6.5 so that 1.0 gram of calcium citrate will neutralize 6.5 mls. 1N acid or 6.5 meq. thereof. Magnesium citrate has an ANC of 3.5 so that 1.0 gram of magnesium citrate will neutralize 3.5 mls. 1N acid or 3.5 meq. thereof. In one embodiment of the present invention where only a two-component formulation is contemplated, calcium carbonate is incorporated in an amount that will contribute from about 20% to about 80% of the total ANC while the calcium citrate portion is incorporated in the tablet in an amount that will contribute from about 80% to about 20% of the total ANC. Preferably, the two will be incorporated in amounts that will each contribute 50% of the total ANC of the dose form.

One preferred embodiment of the present invention is a tripartite system in which calcium carbonate, calcium citrate and calcium phosphate, either di- or tri-basic, are combined in ratios which will achieve the optimal buffering levels both immediately and for sustained periods of time. As before, the amounts of each will comprise a percentage of the total that effectively contributes to the overall ANC of the formulation. The exact amounts in terms of weight percentage will vary depending upon the size of the tablet formulated. The weight amount, however can easily be calculated by one skilled in the art knowing the ratios and the respective ANC's of each component. Preferably, calcium carbonate will be incorporated in an amount that will contribute from about 20% to about 70% of the total ANC. Calcium citrate will be incorporated in an amount that will contribute from about 20% to about 35% of the total ANC of the system while the calcium phosphate, di- or tri-basic, is incorporated in an amount that will contribute from about 20% to 50% of the total ANC of the antacid composition. More preferably, each component will be incorporated in an amount that will contribute from about 30% to about 40% of the total ANC while most preferably each component will be incorporated in an amount that will contribute about one-third of the total ANC of the formulation.

Another preferred embodiment of the present invention is a tripartite system in which calcium carbonate, calcium phosphate, either di- or tri-basic, and magnesium citrate are combined in ratios which will achieve the optimal buffering levels both immediately and for sustained periods of time. As before, the amounts of each will comprise a percentage of the total that effectively contributes to the overall ANC of the formulation. The exact amounts in terms of weight percentage will vary depending upon the size of the tablet formulated. The weight amount, however can easily be calculated by one skilled in the art knowing the ratios and the respective ANC's of each component. Preferably, calcium carbonate will be incorporated in an amount that will contribute from about 20% to about 80% of the total ANC. Magnesium citrate will be incorporated in an amount that will contribute from about 5% to about 30% of the total ANC of the system while the calcium phosphate, di- or tri-basic, is incorporated in an amount that will contribute from about 15% to 50% of the total ANC of the antacid composition. More preferably, magnesium citrate will be incorporated in an amount that will contribute about 8% to about 15% of the total ANC, while the remainder of the ANC will be contributed by calcium carbonate and calcium phosphate, di- or tri-basic.

These formulations then surprisingly and unexpectedly are able to achieve the optimal buffering profile as achieved by dihydroxy aluminum sodium carbonate (DASC) while at the same time providing a source of calcium that is sodium and aluminum free. And despite the presence of this calcium in the system, the additional phosphate that is made available through the calcium phosphate offsets the prevention of phosphate absorption otherwise caused by the calcium. Moreover, the tripartite system allows for an effective acid neutralizing capacity that will produce less gas in the digestive system. The evolution of $CO_2$ gas from the neutralization reaction can naturally cause additional discomfort for obvious reasons, but in the formulations of the present invention, the carbonate level can be reduced with a corresponding increase in the amount of calcium phosphate and calcium citrate so as to provide alternative dose forms for those individuals who are more sensitive to this development. The following Table 1 discloses three tripartite antacid formulations comprising calcium carbonate, calcium citrate, and calcium phosphate. Also disclosed are the relative percent ANC contributions and the weight in milligrams of each component in a standard antacid tablet with a total ANC of 7.5.

TABLE 1

| Acid Neutralization Capacity Percent Contribution cal. carb./cal. cit./cal. phos. | Total Calcium Carbonate | Total Calcium Citrate | Total Calcium Phosphate |
|---|---|---|---|
| a) 37.5/25.0/37.5 | 140.0 mg. | 290.0 mg | 210.0 mg. |
| b) 25.0/25.0/50 | 95.0 mg. | 290.0 mg. | 280.0 mg. |
| c) 50.0/25.0/25.0 | 190.0 mg. | 290.0 mg. | 140.0 mg. |

Formulation b for example, will result in the least amount of gas production since the least amount of calcium carbonate is used in terms of an acid neutralizing component.

Table 2 discloses three tripartite antacid formulations comprising calcium carbonate, calcium citrate, and magnesium citrate. Also disclosed are the relative percent ANC contributions and the weight in milligrams of each component in a standard antacid tablet with a total ANC of 10.9.

TABLE 2

| Acid Neutralization Capacity Percent Contribution cal. carb./cal. cit./cal. phos. | Total Calcium Carbonate | Total Calcium Phospate | Total Magnesium Citrate |
|---|---|---|---|
| a) 67.9/22.9/9.2 | 368.4 mg. | 182.0 mg | 284.1 mg. |
| b) 45.4/45.4/9.3 | 249.5 mg. | 369.6 mg. | 287.6 mg. |

Formulation b for example, will result in the least amount of gas production since the least amount of calcium carbonate is used in terms of an acid neutralizing component.

Along with the actives set forth above, the antacid formulations of the present invention will include a number of carrier materials, and fillers and other minor excipients normally found in most solid and liquid dosage antacid compositions. Optionally, another active such as simethicone may be added to reduce any discomfort resulting from the formation of gas that may accompany the other digestive disorders and is incorporated in amounts well known in the art. Inactive ingredients, for example, may include a bulking agent such as starch, and starch derivatives, cellulose and cellulose derivatives, corn syrup, sugars, sugar alcohols and the like, lubricants such as magnesium stearate and mineral oil, tableting agents such as polyethylene glycol and titanium dioxide, silica, assorted F.D.& C. dyes, flavors, high intensity sweeteners and the like. The exact types and amounts of these ingredients are well known and can be readily determined by one skilled in the art.

The antacid formulations of the present invention were effective in providing upfront and long lasting relief of stomach heartburn, acid indigestion and sour stomach through the reduction in stomach acidity to a pH of from about 3.0 to about 5.0. The effectiveness of these formulations was borne out by what is known in the art as the Modified Rosset Rice procedure or the Acid Challenge test whereby the pH of a system treated with a particular formulation is measured over time. Under this procedure, twenty (20) milliequivalents (megs.) of the antacid formulation to be tested are mixed with ten (10) meg. of acid (100 mls. of 0.1M HCl). This is mixed thoroughly and the pH is monitored as an additional one (1) ml. of the 0.1M HCl is added per minute. The measured pH is recorded at regular intervals and plotted as a function of time.

Referring now to the drawings, FIG. 1 depicts the continuous acid challenge profiles of five (5) calcium carbonate/calcium citrate formulations over a 2 hour period. All five formulations maintained pH values in the in-vitro system from about 2.9 to about 5.1. Increasing the citrate to carbonate ratio improves the kinetics of the buffering system, providing the optimal pH (3–5) more rapidly without compromising the duration of neutralization.

Figure 2:
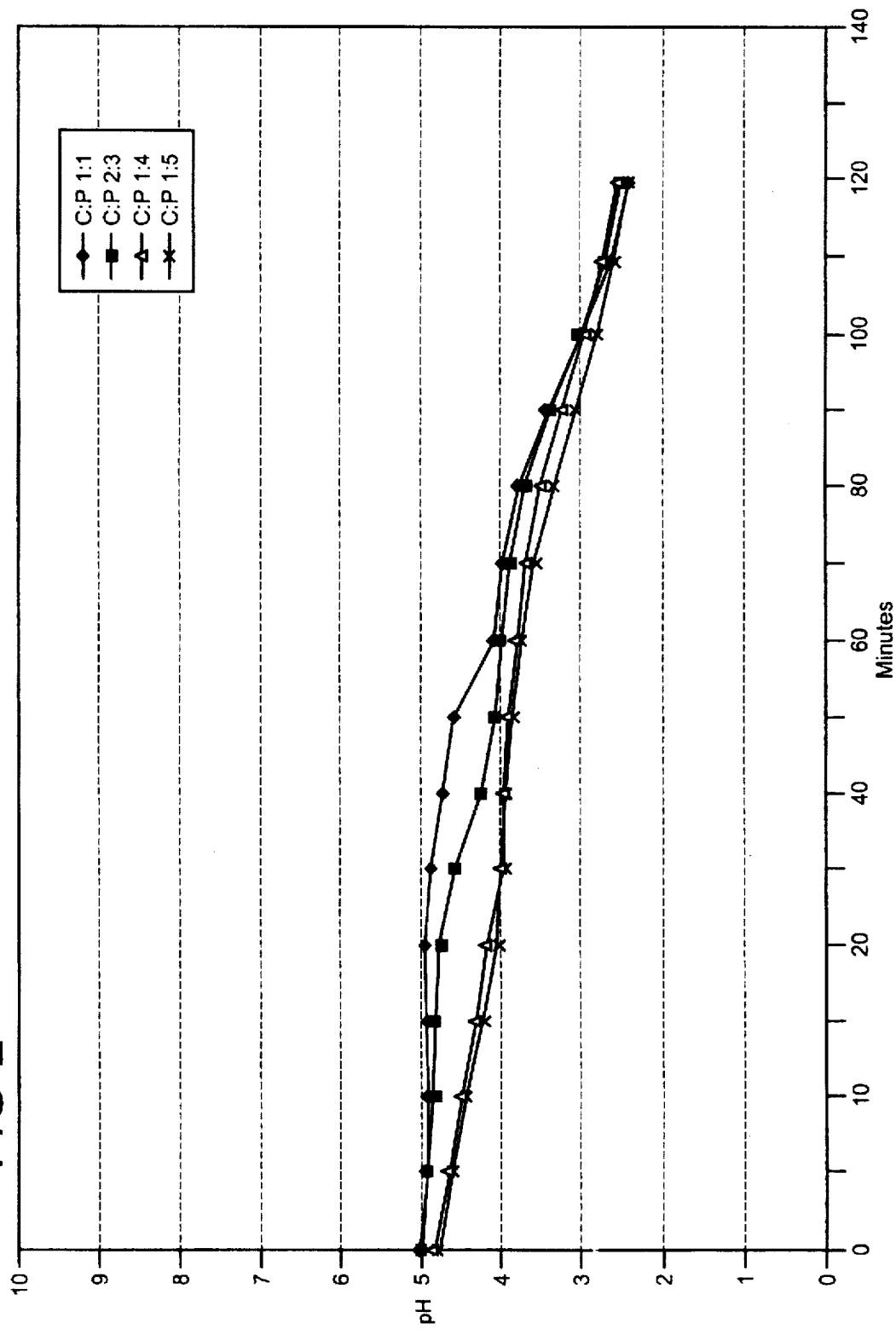
FIG. 2 is a graph depicting the continuous acid challenge profile of calcium carbonate/calcium phosphate formulations of the present invention as a function of pH versus time.

Referring now to FIG. 2, four formulations comprising calcium carbonate/tri-basic calcium phosphate were challenged at various weight ratio amounts. A similar increase in buffering kinetics to that discussed in FIG. 1 was observed when the ratio of phosphate to carbonate was increased.

Figure 3:
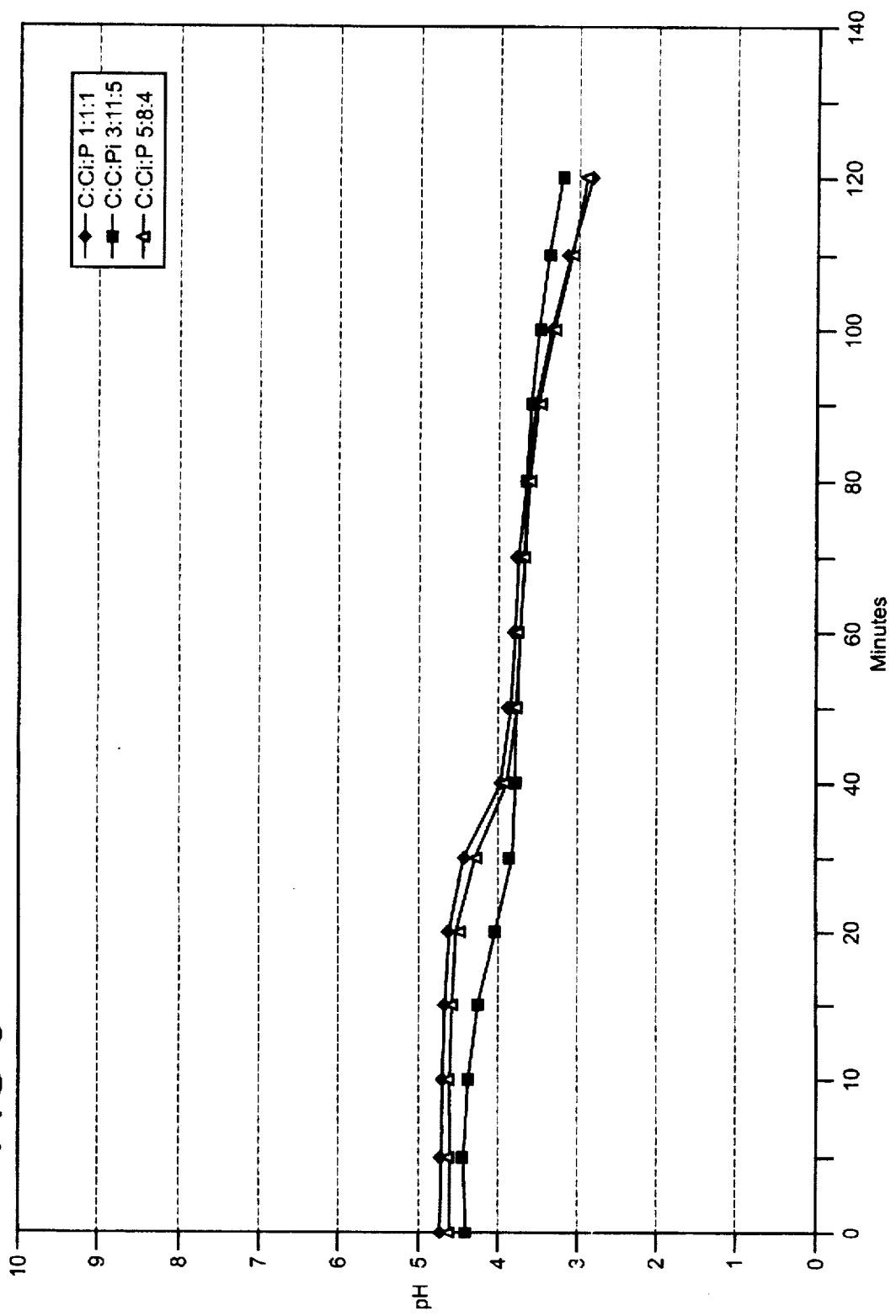
FIG. 3 is a graph depicting the continuous acid challenge profile of calcium carbonate/calcium citrate/tri-calcium phosphate formulations of the present invention as a function of pH versus time.

FIG. 3 shows the result for a tripartite formulation comprising calcium carbonate/calcium citrate/tri-basic calcium phosphate in three different ratios. Whereas the optimal pH range of 3.0 to 5.0 was fairly well established and maintained (i.e. 2.9 to 4.7) all three formula ratios provided substantially similar results.

Figure 4:
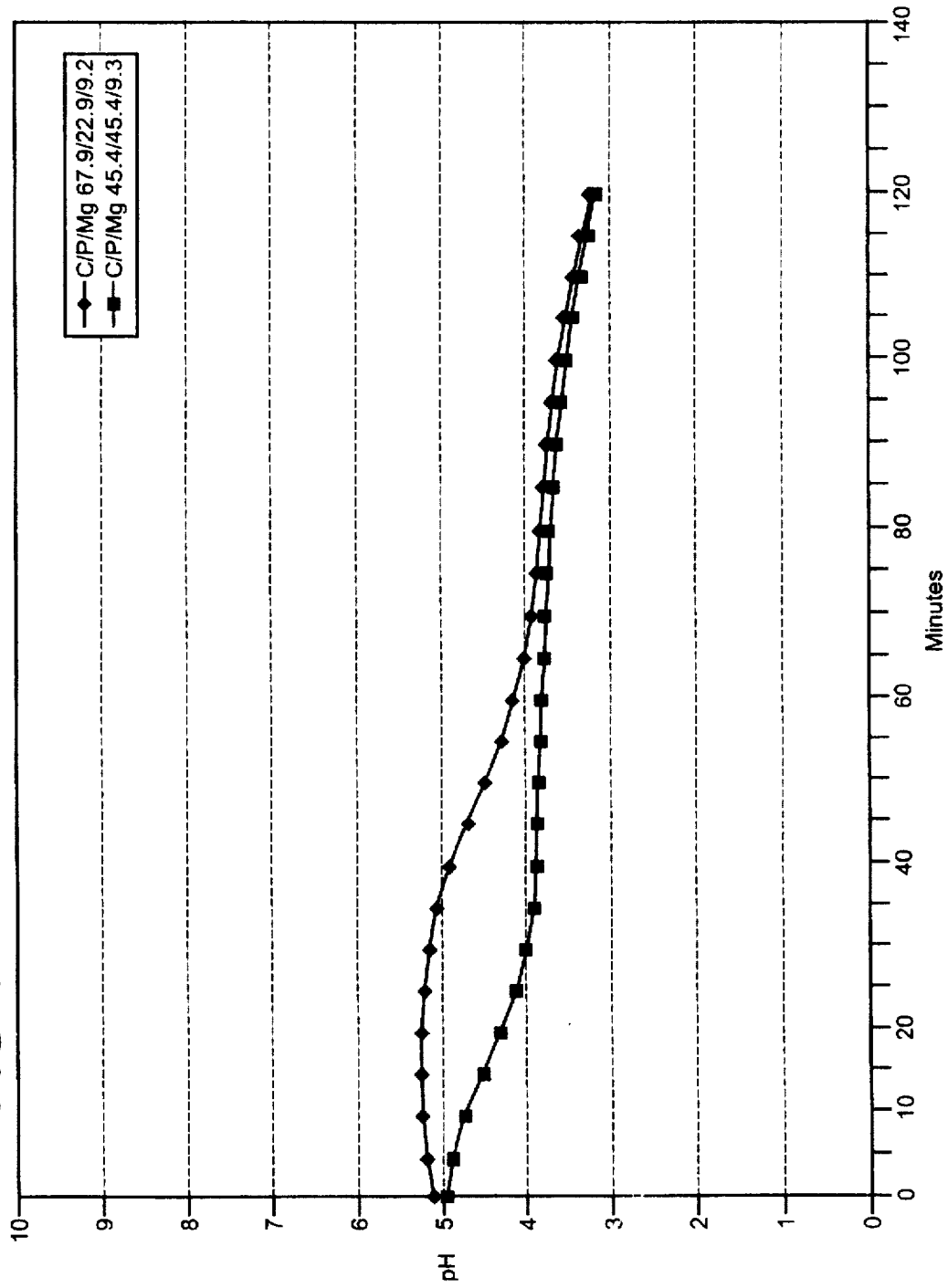
FIG. 4 is a graph depicting the continuous acid challenge profile of calcium carbonate/calcium phosphate/magnesium citrate formulations of the present invention as a function of pH versus time.

FIG. 4 shows the result for a tripartite formulation comprising calcium carbonate/magnesium citrate/tri-basic calcium phosphate in three different ANC ratios. Whereas the optimal pH range of 3.0 to 5.0 was fairly well established and maintained (i.e. 3.1 to 5.2) both formula ratios provided substantially similar results.

Obviously, numerous variations in ANC ratios and other components may be made which will alter in a minor fashion the make-up of the antacid formulations described herein. Those described above are for illustrative purposes only, and it is acknowledged that many others are possible which are still considered to fall within the spirit and scope of the present invention as recited by the following claims.

What we claim is:

1. An antacid pharmaceutical composition for the immediate and long lasting relief of gastrointestinal distress comprising a first active agent which is calcium carbonate, and a second active agent which is selected from the group consisting of calcium citrate, calcium phosphate and mixtures thereof, wherein the ratio of said first active agent to the second active agent is from about 20:80 to about 80:20, inactive carrier materials and excipients.

2. The antacid composition of claim 1 wherein said second active agent consists of calcium citrate.

3. The antacid composition of claim 1 wherein said second active agent consists of calcium phosphate.

4. The antacid composition of claim 1 further comprising a third active agent which is magnesium citrate.

5. The antacid composition of claim 1 wherein said second active agent consists of calcium citrate and calcium phosphate, and wherein the ratio of said calcium carbonate, calcium citrate and calcium phosphate is from about 60:20:20 to about 20:35:45.

6. The antacid composition of claim 5 wherein the ratio is about 30:30:40.

7. The antacid composition of claim 4 wherein said calcium carbonate, calcium phosphate and magnesium citrate are present in a ratio of from about 80:15:5 to about 20:50:30.

8. The antacid composition of claim 6 wherein the ratio is about 45:45:10.

9. The antacid composition of claim 1 wherein said inactive carrier materials are selected from the group consisting celluloses, starches, sugars, sugars alcohols, silicates, corn syrup, silica, mineral oil, polyethylene glycol, talc and mixtures thereof.

10. The antacid composition of claim 1 wherein said excipients are selected from the group consisting of tabletting agents, lubricating agents, simethicone, artificial high intensity sweeteners, F.D. & C. food colors, flavors and mixtures thereof.

11. The antacid composition of claim 1 prepared as a chewable tablet dosage form.

12. The antacid composition of claim 1 prepared as a liquid dosage form.

13. A low sodium antacid and dietary calcium supplement comprising calcium carbonate, calcium citrate, calcium phosphate, carrier materials excipients and fillers.

14. The antacid composition of claim 13 wherein said calcium carbonate, calcium citrate and calcium phosphate are incorporated into the composition in amounts that are effective in contributing to the total acid neutralization capacity in ratios of from about 60:20:20 to about 10:35:45, respectively.

15. The antacid composition of claim 14 wherein said calcium carbonate, calcium citrate and calcium phosphate are incorporated into the composition in amounts that are effective in contributing to the total acid neutralization capacity of the composition in a ratio of about 30:30:40, respectively.

16. A low sodium antacid and dietary calcium supplement comprising calcium carbonate, calcium phosphate, magnesium citrate, carrier materials, excipients and fillers.

17. The antacid composition of claim 16 wherein said calcium carbonate, calcium phosphate and magnesium citrate are incorporated into the composition in amounts that are effective in contributing to the total acid neutralization capacity of the composition in a ratio of about 80:15:5 to about 20:50:30, respectively.

18. The antacid composition of claim 17 wherein said calcium carbonate, calcium phosphate and magnesium citrate are incorporated into the composition in amounts that are effective in contributing to the total acid neutralization capacity of the composition in a ratio of about 45:45:10.

19. The antacid composition of claim 14 or claim 18 wherein said carrier materials are selected from the group consisting of cellulose, cellulose derivatives, starches, sugars, sugar alcohols, silicates, polyethyleneglycol, talc and mixtures thereof.

20. The antacid composition of claim 19 wherein said excipients are selected from the group consisting of tabletting agents, lubricating agents, artificial high intensity sweeteners, F.D. & C. food colors, flavors and mixtures thereof.

21. The antacid composition of claim 20 prepared as a chewable tablet dosage form.

22. The antacid composition of claim 20 prepared as a liquid dosage form.

* * * * *